United States Patent [19]

Porath-Furedi

[11] 4,055,491

[45] Oct. 25, 1977

[54] APPARATUS AND METHOD FOR REMOVING FINE PARTICLES FROM A LIQUID MEDIUM BY ULTRASONIC WAVES

[76] Inventor: Asher Porath-Furedi, 10 Kubovy St., Jerusalem, Israel

[21] Appl. No.: 691,982

[22] Filed: June 2, 1976

[51] Int. Cl.² .................... B01D 35/20; B03D 3/06; C02B 1/80

[52] U.S. Cl. .................................. 210/19; 47/1.4; 47/DIG. 12; 209/5; 210/513; 210/521; 210/DIG. 22; 210/DIG. 23

[58] Field of Search ......... 210/19, 513, 521, DIG. 22, 210/DIG. 23; 209/1, 5; 47/1.4, DIG. 12

[56] References Cited

U.S. PATENT DOCUMENTS

| | | | |
|---|---|---|---|
| 2,514,471 | 7/1950 | Calhoun | 210/19 |
| 2,907,455 | 10/1959 | Sasaki | 210/DIG. 22 |
| 3,305,481 | 2/1967 | Peterson | 210/19 |
| 3,489,679 | 1/1970 | Davidson et al. | 210/19 |
| 3,499,437 | 3/1970 | Balamuth | 47/1.3 X |
| 3,511,380 | 5/1970 | Rice et al. | 210/521 X |
| 3,782,547 | 1/1974 | Dietert | 210/19 X |
| 3,898,164 | 8/1975 | Hsiung | 210/521 |

Primary Examiner—Joseph Scovronek
Attorney, Agent, or Firm—Benjamin J. Barish

[57] ABSTRACT

Apparatus and method are described for using ultrasonic waves for removing microscopic particles from a liquid medium, such as algae from a solar or refuse pond, or blood cells from blood. The described apparatus includes an ultrasonic generator propagating ultrasonic waves of over one megacycle per second through the liquid medium to cause the flocculation of the microscopic particles at spaced points. In two described embodiments, the ultrasonic waves are propagated in the horizontal direction through the liquid medium, and baffle plates are disposed below the level of propagation of the ultrasonic waves. The baffles are oriented to provide a high resistance to the horizontal propagation therethrough of the ultrasonic waves and a low-resistance to the vertical settling therethrough of the flocculated particles. The ultrasonic generator is periodically energized to flocculate the particles, and then de-energized to permit the settling of the flocculated particles through the baffle plates from whence they are removed.

10 Claims, 3 Drawing Figures

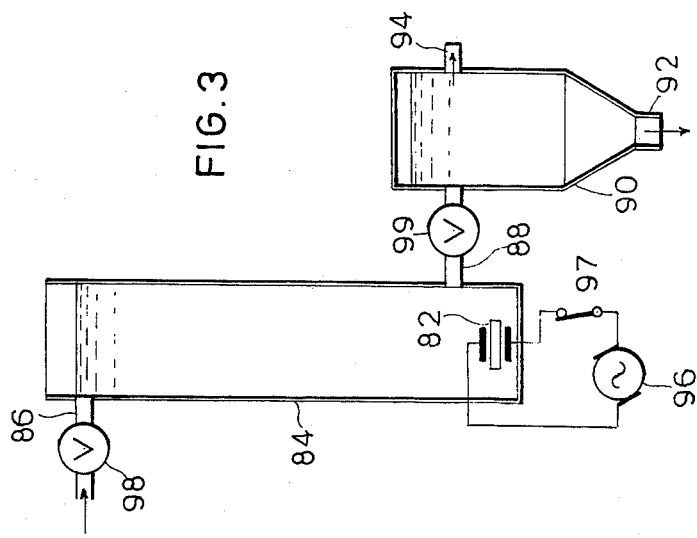
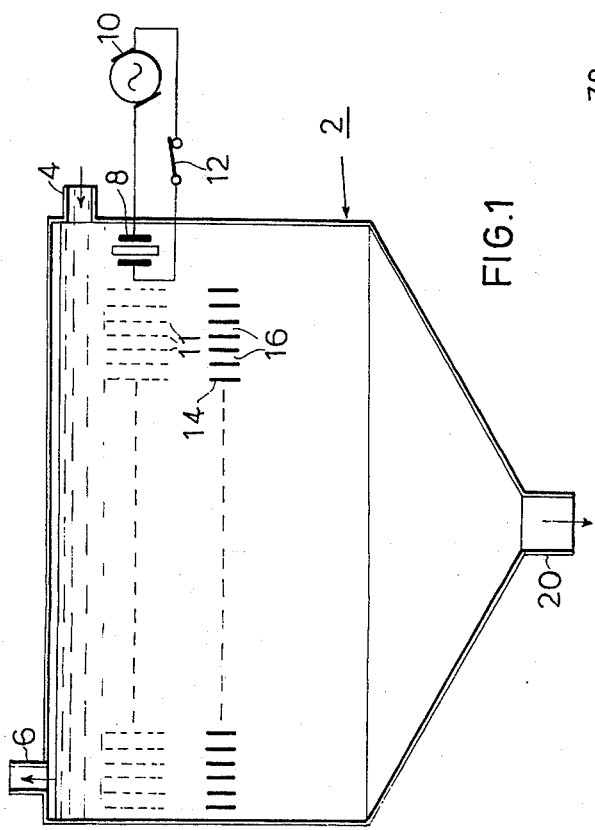
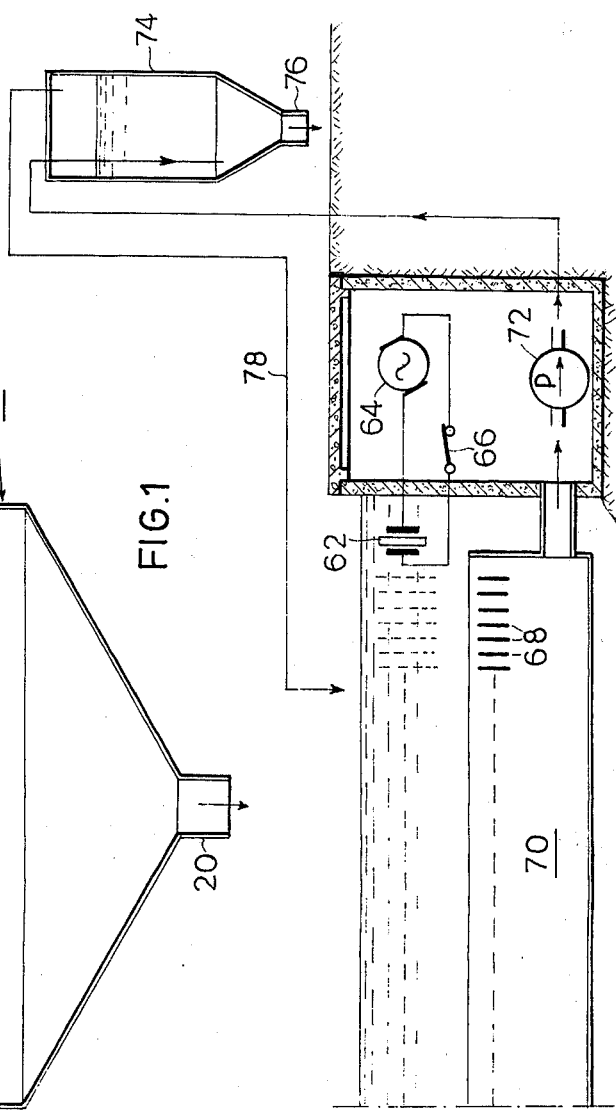

APPARATUS AND METHOD FOR REMOVING FINE PARTICLES FROM A LIQUID MEDIUM BY ULTRASONIC WAVES

BACKGROUND OF THE INVENTION

The present invention relates to apparatus and to a method for removing fine particles from a liquid medium. The invention is particularly useful for removing single cell or filamentous microscopic particles in the order of up to 10 microns in diameter. One desicribed application is for removing algae growing in a solar or sludge pond, and another described application is for removing blood cells from blood.

The conventional separation techniques, such as filtering or centrifuging, are generally not efficient and/or are very expensive when used for large-scale separation of particles of microscopic size (e.g., in the order of up to 10 microns in diameter) suspended in a liquid medium. Various sonic or compressional wave techniques have been used for particle separation, but as a rule they have been used for particles much larger than microscopic size.

An objecct of the present invention is to provide novel apparatus and method for removing single cell or filamentous particles of microscopic size, in the order of up to 10 microns in diameter, from a liquid medium by ultrasonic waves.

SUMMARY OF THE INVENTION

According to one aspect of the present invention, there is provided apparatus for removing fine particles from a liquid medium comprising: a container for the particle-containing liquid medium; an ultrasonic generator oriented to propagate ultrasonic waves through the liquid medium to cause the flocculation of the particles at spaced points in the direction of propagation of the ultrasonic waves; means for periodically energizing the ultrasonic generator to cause the flocculation of the particles and for de-energizing the generator to permit the settling of the flocculated particles by gravity; and means for removing the settled flocculated particles.

The ultrasonic waves are propagated in a horizontal direction through the liquid medium, and baffle means are disposed below the level of the propagated ultrasonic waves to provide a high resistance to the horizontal propagation therethrough of the ultrasonic waves, and a lower resistance to the vertical settling therethrough of the flocculated particles. The settled flocculated particles are removed from below the baffle means.

Very short periods of time, in the order of tens of seconds, and very little electrical energy, in the order of tens of watts, are required to flocculate the particles. The invention thus provides an efficient and low cost technique for the separation of fine particles.

Several embodiments and applications of the invention are described below. In one embodiment, the container is a conventional receptacle receiving the liquid containing the particles to be separated, one application for this embodiment being for the separation of blood cells from blood. In a second described embodiment, the container is a pond containing water and algae growing therein and to be separated therefrom. Possible applications for this embodiment include the treatment of refuse by growing algae in sludge ponds, and the production of fuel or protein food from algae grown in ponds, one of the serious problems in exploiting these techniques of refuse treatment and algae cultivation being the efficient and low-cost separation of the algae from the ponds.

Further features, advantages, and possible applications of the invention will be apparent from the description below.

BRIEF DESCRIPTION OF THE DRAWINGS

The invention is herein described, by way of example only, with reference to two preferred embodiments illustrated in the accompanying drawings, wherein:

FIG. 1 diagrammatically illustrates one form of apparatus constructed in accordance with the invention for use in separating microscopic-size particles from a liquid medium, such as blood cells from blood;

FIG. 2 illustrates the invention embodied in a pond for growing and separating algae, for possible application in treating refuse, or growing algae for fuel or protein production, as mentioned above; and FIG. 3 illustrates a further form of the apparatus including a vertical receptacle.

DESCRIPTION OF THE PREFERRED EMBODIMENTS

With referencce first to FIG. 1, there is shown a receptacle 2 having an inlet 4 for the liquid containing the particles to be separated. As one example, the liquid may be human blood, in which case the microscopic particles to be separated are the red blood cells (about 7 microns in diameter), the blood plasma remaining being removed from the receptacle via an outlet 6.

An ultrasonic wave generator 8, such as an electrically-energized piezoelectric crystal, is disposed within receptacle 2 below its upper surface so as to be submerged by the liquid introduced into the tank. Generator 8 is driven by an oscillator 10 and is energized and deenergized by an electrical switching device, schematically shown at 12, which may be a cyclically operated mechanical switch, electronic switch, or the like.

When ultrasonic generator 8 is energized, it propagates ultrasonic compressional waves through the liquid medium within the receptacle in a horizontal direction. This causes the flocculation or coagulation of the microscopic particles within the liquid medium at spaced points 11 in the direction of propagation.

More particularly, generator 8 produces standing compressional waves having high-pressure nodes at the spaced points 11 along the direction of propagation of the wave equal to one-half the wave length. Particles in the liquid medium which are smaller than one-half the wave length of the compressional waves are subjected to a force vector which is the resultant of the forces acting on it from the standing wave, and which acts to move the particles to the closest high-pressure node. Thus, particles tend to populate (i.e., bunch, or flocculate) at the high-pressure nodes 11 and depopulate the spaces between the nodes. When the microscopic particles are blood cells or algae, it has been found that the flocculated particles adhere to each other and form wafer-like pellets which settle by gravity when the ultrasonic generator is de-energized.

The system of FIG. 1 further includes baffle means disposed in the liquid medium below the level of propagation of the ultrasonic waves, which baffle means provides a high resistance to the horizontal propagation therethrough of the ultrasonic waves, and a low resistance to the vertical settling therethrough of the populated particles. The baffle means in FIG. 1 are shown as vertical plates 14 horizontally spaced from each other by spaces 16.

Thus, by periodically energizing the ultrasonic generator, the particles in the liquid medium are caused to flocculate, and then by periodically de-energizing the generator, the flocculated particles are permitted to settle by gravity through the baffle plates 14, from whence they may be conveniently removed via outlet 20.

Where the particles to be removed are of microscopic size, for example 10 microns in diameter or smaller, the frequency of the ultrasonic wave generator should be at least one megacycle per second, but in any event, sufficiently high so that one-half its wave length is greater than the diameter of the microscopic particles to be removed.

In the case of removing red blood cells from human blood (the blood cells having a diameter of about 7 microns), it has been found that a frequency of about 2–3 megacycles per second should be used, a frequency of 2.7 megacycles per second having been found particularly effective. In this example, the receptacle 2 may have a length of about 1 meter; the generator 8 may have a verticla height of about 5 cm; and the baffle plates 14 may have a height of about 1 cm and a horizontal spacing 16 of about 1 mm. Preferably, the upper edge of the baffle plate is within about one-half the vertical height of the generator, or about 2.5 cm in the described example. The period of energization of the generator (e.g., a piezoelectric crystal) may be about 20 seconds, and the period of deenergiztion, for permitting the flocculated particles to settle through the baffle plates), may each be about 5 seconds.

FIG. 2 illustrates the invention embodied in a system for removing algae growing in a pond. This application is particularly of potential commercial importance because of recent work directed towards the utilization of solar energy for growing algae, particularly *Dunaliella*, in solar ponds for producing fuel, and for growing other algae in other ponds for producing food protein, one of the serious problems not heretofore solved being the efficient and low-cost removal of the algae from the ponds. Another possible application is in the reclamation of water and/or protein from refuse wherein, according to one system, algae is grown in a sludge pond and must be separated therefrom in order to reclaim the water and/or protein.

The pond illustrated in FIG. 2 is generally designated 60 and may be a natural pond, or an artificially created one, filled with water exposed to solar radiations. Where the algae is to be grown and harvested for fuel or protein production, the pond would be a solar pond filled with salt water; and where water (or protein) is to be reclaimed, it would be a sewage pond. It has been found that the growth of algae can be promoted in the pond usually at a level slightly below the upper surface of the pond. The ultrasonic wave generator 62 would be immersed in the pond at the level of growth of the algae to propagate ultrasonic waves in the horizontal direction. The generator is driven by an oscillator 64 and its energization and deenergization are controlled by a switch 66, as described above with respect to FIG. 1.

Below the level of propagation of the ultrasonic waves are the baffle plates 68 having a high resistance to the horizontal propagation therethrough of the ultrasonic waves, and a lower resistance to the vertical settling therethrough of the flocculated algae particles. The latter settle in a chamber 70 below the baffle plates 68, and are pumped via pump 72 to a settling tank 74. The flocculated particles settle at the bottom of the tank and are removed via the lower outlet 76. The water at the top of the tank is removed via a condiut 78 and may be reintroduced back into the pond 60. The algae in the above application have a diameter of 5–9 microns; the frequency of the ultrasonic generator 62 is therefore preferably about 2.8 megacycles per second.

FIG. 3 illustrates a further embodiment wherein the ultrasonic wave generator 82 is disposed at the bottom of a vertical column 84 having an inlet 86 at the top of the column, and an outlet 88 at the bottom of the column just above the generator. The outlet leads to a separation tank 90 having a lower outlet 92 for the flocculated particles and an upper outlet 94 for the remaining liquid medium. Generator 82 is oriented to propagate ultrasonic waves in the vertical direction through the liquid medium in column 84. The generator is driven by an oscillator 96 controlled by a switch 97. When the generator is energized, the particles are flocculated at vertically spaced points, and when it is deenergized, the flocculated particles settle in tank 90 and are removed via the lower outlet 92. The system of FIG. 3 is preferably operated as a batch process by suitably controlling the tank inlet and outlet valves 98 and 99.

Many other variations, modifications and applications of the illustrated embodiments of the invention will be apparent.

What is claimed is:

1. Apparatus for removing fine particles from a liquid medium, comprising: a container for the particle-containing liquid medium; an ultrasonic generator oriented to propagate ultrasonic waves through the liquid medium to cause the flocculation of the particles at spaced points in the direction of propagation of the ultrasonic waves; means for periodically energizing the ultrasonic generator to cause the flocculation of the particles and for deenergizing the generator to permit the settling of the flocculated particles by gravity; and means for removing the settled flocculated particles; said ultrasonic generator being oriented to propagate the ultrasonic waves through the liquid medium in a horizontal direction at a prdetermined level thereof; said apparatus further including baffle means disposed in the liquid medium below the level of the propagated ultrasonic waves; said baffle means providing a high resistance to the horizontal propagation therethrough of the ultrasonic waves, and a low resistance to the vertical settling therethrough of the flocculated particles; the settled flocculated particles being removed from below the baffle means.

2. Apparatus according to claim 1, wherein said baffle means comprises a plurality of vertically-extending horizontally-spaced baffle plates.

3. Apparatus according to claim 1, wherein said container is a tank receiving the liquid-containing particles to be separated therefrom.

4. A method of removing microscopic particles from a liquid medium comprising the steps of: propagating ultrasonic waves in the horizontal direction at a frequency of over one megacycle per second through the liquid medium to cause the flocculation of the particles at spaced points in the direction of propagation of the ultrasonic waves; discontinuing the propagation of the ultrasonic waves to permit the settling by gravity of the flocculated particles through baffle means disposed below the level of propagation of the ultrasonic waves which baffle means provides a high resistance to the horizontal propagation therethrough of the ultrasonic waves and a low resistance to the vertical settling therethrough by gravity of the flocculated particles; periodically repeating propagating and discontinuing the propagation of the ultrasonic waves to periodically flocculate and then settle the particles; and removing the settled flocculated particles.

5. The method according to claim 4, wherein the ultrasonic waves are periodically propagated through the liquid medium at a frequency of over 2 megacycles per second.

6. The method according to claim 4, wherein the liquid is a pond, and the microscopic particles removed therefrom are algae growing in the pond.

7. The method according to claim 6, wherein said pond is a solar pond including salt water irradiated by the sun for promoting the growth of the algae therein.

8. The method according to claim 6, wherein said pond is a sewage pond including the algae growing therein.

9. The method according to claim 4, wherein the liquid is blood, and the microscopic particles removed therefrom are red blood cells.

10. The method according to claim 4, wherein the periods of propagation of the ultrasonic wave are about 20 seconds each.

* * * * *